(12) United States Patent
Schabbach et al.

(10) Patent No.: US 10,786,430 B2
(45) Date of Patent: Sep. 29, 2020

(54) MEDICAMENT DELIVERY DEVICE

(71) Applicant: SANOFI-AVENTIS DEUTSCHLAND GMBH, Frankfurt am Main (DE)

(72) Inventors: Michael Schabbach, Frankfurt am Main (DE); Daniel Auernhammer, Frankfurt am Main (DE); Christoph Dette, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 288 days.

(21) Appl. No.: 15/541,120

(22) PCT Filed: Jan. 15, 2016

(86) PCT No.: PCT/EP2016/050815
§ 371 (c)(1),
(2) Date: Jun. 30, 2017

(87) PCT Pub. No.: WO2016/113409
PCT Pub. Date: Jul. 21, 2016

(65) Prior Publication Data
US 2017/0354570 A1     Dec. 14, 2017

(30) Foreign Application Priority Data
Jan. 16, 2015   (EP) ..................................... 15151364

(51) Int. Cl.
*A61J 1/14*       (2006.01)
*A61M 5/315*      (2006.01)
*A61M 5/31*       (2006.01)

(52) U.S. Cl.
CPC ........ *A61J 1/1468* (2015.05); *A61M 5/31513* (2013.01); *A61M 5/31515* (2013.01);
(Continued)

(58) Field of Classification Search
CPC .. A61J 1/1468; A61J 1/1406; A61M 5/31513; A61M 5/31583; A61M 2005/5126; B65D 51/00
(Continued)

(56) References Cited

U.S. PATENT DOCUMENTS 6,004,300 A      12/1999  Butcher et al.
2003/0233075 A1* 12/2003  Huegli ............. A61M 5/31513
                                                    604/222
(Continued)

FOREIGN PATENT DOCUMENTS

EP    0925798       6/1999
JP    2014-505503   3/2014
(Continued)

OTHER PUBLICATIONS

International Preliminary Report on Patentability in International Application No. PCT/EP2016/050815, dated Jul. 18, 2017, 8 pages.
(Continued)

*Primary Examiner* — Philip R Wiest
(74) *Attorney, Agent, or Firm* — Fish & Richardson P.C.

(57) ABSTRACT

The disclosure relates to a medicament delivery device, comprising a medicament cartridge adapted to contain a medicament and a stopper slidably arranged within the cartridge. The stopper-comprises a rigid body that is enclosed partially by a soft sealing component.

19 Claims, 2 Drawing Sheets

(52) U.S. Cl.
CPC ......... *A61J 1/1406* (2013.01); *A61M 5/31551* (2013.01); *A61M 5/31583* (2013.01); *A61M 2005/3126* (2013.01); *A61M 2205/0216* (2013.01); *A61M 2205/58* (2013.01)

(58) Field of Classification Search
USPC .......................................... 604/218, 403–416
See application file for complete search history.

(56) References Cited

U.S. PATENT DOCUMENTS

| | | | |
|---|---|---|---|
| 2007/0219507 A1* | 9/2007 | Dai ................... | A61M 5/31511 604/218 |
| 2009/0299288 A1* | 12/2009 | Sie .................... | A61M 5/14566 604/151 |
| 2010/0204658 A1* | 8/2010 | Imai ................. | A61M 5/31513 604/222 |
| 2015/0302778 A1* | 10/2015 | Helmer ................. | G09B 23/28 604/230 |

FOREIGN PATENT DOCUMENTS

| WO | WO 2005/099793 | 10/2005 |
|---|---|---|
| WO | WO 2007/118907 | 10/2007 |
| WO | WO 2008/127345 | 10/2008 |
| WO | WO 2009/001600 | 8/2010 |
| WO | WO 2010/125400 | 11/2010 |
| WO | WO 2012/076494 | 6/2012 |
| WO | WO 2013/064590 | 5/2013 |
| WO | WO 2014/001386 | 1/2014 |

OTHER PUBLICATIONS

International Search Report and Written Opinion in International Application No. PCT/EP2016/050815, dated May 2, 2016, 11 pages.

\* cited by examiner

MEDICAMENT DELIVERY DEVICE

CROSS-REFERENCE TO RELATED APPLICATIONS

This application is a U.S. national stage application under 35 USC § 371 of International Application No. PCT/EP2016/050815, filed on Jan. 15, 2016, which claims priority to European Patent Application No. 15151364.5, filed on Jan. 16, 2015, the entire contents of which are incorporated herein by reference.

TECHNICAL FIELD

The disclosure relates to a medicament delivery device.

BACKGROUND

Medicament delivery devices which are capable of delivering medicaments from a medicament cartridge are well known. Typically, a user must provide energy to drive a medicament through a needle. In case of a manually operable device, this is done by a stopper that has to be continuously pressed during the injection. The stopper is usually made from a soft material, e.g. natural rubber or synthetic rubber. However, the soft material of the stopper may cause dose accuracy problems, respectively when delivering high concentrated medicaments, such as insulin with a concentration of more than 100 insulin units/ml. Injection forces may be too high for the user, in particular if the patient is elderly or has dexterity problems. In this case, the user might deliver an underdose or an overdose resulting in health risks, e.g. Hypoglycemia.

US 2003/233075 A1 describes a piston stopper for an injection device, wherein the piston stopper includes a stopper body manufactured from an inflexible material and a stopper body holder detachably connected to it. A membrane body is placed like a cap onto the stopper body, wherein the membrane is formed from an elastic material.

Furthermore, US 2007/219507 A, US 2009/299288 A, US 2009/312716 A and US 2013/041344 A describe piston stoppers for injection devices.

Thus, there remains a need for an improved medicament delivery device.

SUMMARY

In some embodiments, a medicament delivery device comprises a medicament cartridge adapted to contain a medicament and a stopper slidably arranged within the cartridge. According some embodiments, the stopper comprises a rigid body that is enclosed partially by a soft sealing component.

The rigid body reduces the elasticity of the stopper compared to a soft stopper and thus allows reduced injection forces required to drive the medicament from the cartridge through a needle and a better dose accuracy as well as a shorter injection times compared to the state of the art. This is particularly useful if a high concentrated medicament, such as insulin with a concentration of more than 100 insulin units, has to be delivered in small dose volume increments.

In an exemplary embodiment, the rigid body of the stopper is made from a hard plastic material such as polypropylene (e.g., Borealis Bormed™ BE860MO, Borealis Bormed™ BH348MO, Borealis Bormed™ DM55pharm, Borealis Bormed™ HD810MO, Borealis Bormed™ HD850MO, Borealis Bormed™ HF840MO, Borealis Bormed™ HF855MO, Borealis Bormed™ RB801CF, Borealis Bormed™ RD804CF, Borealis Bormed™ RD808CF, Borealis Bormed™ RE806CF, Borealis Bormed™ RF825MO, Borealis Bormed™ RF830MO, Borealis Bormed™ RG835MO, Borealis Bormed™ SC820CF, Borealis Bormed™ TD109CF), polyethylene (e.g., high-density polyethylene (HDPE), such as e.g. PE GF 4760), polyoxymethylene, polyamide or cyclo olefin copolymer (e.g. Zeon Chemical's Zeonex™).

Furthermore, a diameter of the rigid body is smaller than an inner diameter of the cartridge. Thus, the rigid body alone cannot seal against an inner wall of the cartridge. This allows the arrangement of the soft sealing component, wherein the soft sealing component comprises at least one sealing portion that forms a ring around the circumference of the rigid body for a slidable, fluid-tight engagement of the stopper within the cartridge.

In an exemplary embodiment, the soft sealing component comprises two sealing portions, each forming a ring around the circumference of the rigid body, wherein the sealing portions are spaced from each other in the direction of a longitudinal axis of the cartridge. The sealing portions enable a local elasticity of the stopper just for a required sliding movement of the stopper within the cartridge. The ring-shaped arrangement of the sealing portions compared to a full soft cover of the rigid body maintains the advantage of low injection force, because there is a reduced contact area between the stopper and a cartridge inner wall compared to a stopper that is made completely by a soft rubber material. This requires less injection forces, so that the injection process is user-friendly in particular if the patient is elderly.

In an exemplary embodiment, the soft sealing component comprises two sealing portions, each forming a ring around the circumference of the rigid body, wherein the sealing portions are spaced from each other in the direction of a longitudinal axis of the cartridge and the surface where the soft sealing component is contacting the rigid material in a groove which has a slope versus the longitudinal axis. Said groove having said slope ensures freedom to move for the soft sealing component and optimum positioning and constant friction force.

In an exemplary embodiment, the soft sealing component is made from or comprises a resilient material such as natural rubber or synthetic rubber. Some examples are punched o-rings from bromobutyl compound or injection molded o-rings made of thermoplastic styrene block copolymers.

In a further exemplary embodiment, the cartridge is made from or comprises glass.

In an exemplary embodiment, an inner wall of the medicament cartridge is coated with a sliding layer enabling an easy sliding of the stopper within the cartridge.

In an exemplary embodiment, the sliding layer comprises silicon oil.

Further scope of applicability of the present invention will become apparent from the detailed description given hereinafter. However, it should be understood that the detailed description and specific examples, while indicating exemplary embodiments, are given by way of illustration only, since various changes and modifications within the spirit and scope of the invention will become apparent to those skilled in the art from this detailed description.

BRIEF DESCRIPTION OF THE FIGURES

Exemplarily embodiments will become more fully understood from the detailed description given herein below and the accompanying drawing that is given by way of illustration only, and thus, is not limitative of the present invention, and wherein.

DETAILED DESCRIPTION

Figure 1:
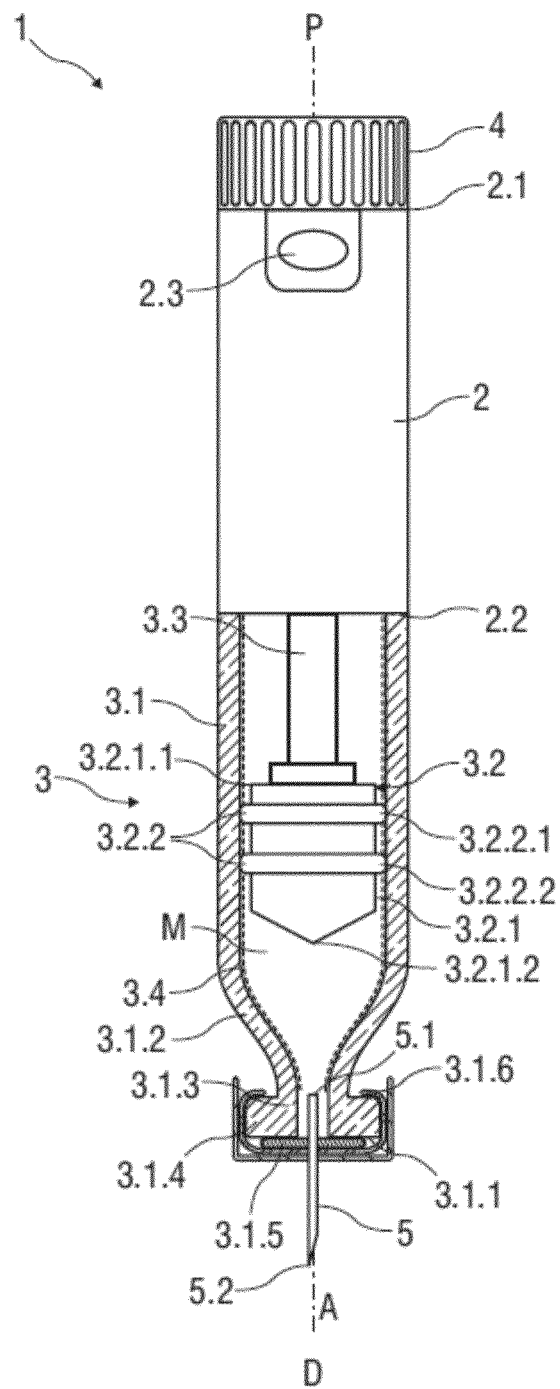
FIG. 1 is a schematic longitudinal section of an exemplary embodiment of a medicament delivery device.

FIG. 1 is a schematic longitudinal section of an exemplary embodiment of a medicament delivery device 1 with a longitudinal axis A extending from a proximal direction P to a distal direction D. The shown medicament delivery device 1 may be designed as an injection pen device.

In an exemplary embodiment, the medicament delivery device 1 comprises a case 2 that is adapted to receive a pre-filled medicament cartridge 3.

The case 2 extends from a proximal end 2.1 to a distal end 2.2 and is of a substantially cylindrical shape. In an exemplary embodiment, the case 2 comprises a dose window 2.3 presenting a set dose of a medicament M, i.e. high concentrated insulin, contained in the medicament cartridge 3. In an exemplary embodiment, the dose is settable by operating a dial knob 4. The dial knob 4 is coupled to the case 2 on its proximal end 2.1. The dial knob 4 is rotatable around the longitudinal axis A with respect to the case 2, whereby a dose is set by turning the dial knob 4 in a predetermined direction about the longitudinal axis A. Alternatively, the medicament delivery device 1 may be configured for administering a fixed dose of the medicament M without having to turn the dial knob 4.

The medicament cartridge 3 is coupled to the case 2 with respect to movement in the proximal direction P and the distal direction D. The medicament cartridge 3 may be releasably connected to or retained fixed to the case 2.

The medicament cartridge 3 comprises a cartridge body 3.1 that may be made from glass and adapted to contain the medicament M, e.g. high concentrated insulin. The cartridge body 3.1 is designed as a generally tubular barrel with a not shown open proximal end and a distal end 3.1.1, e.g. defined by an inwardly converging shoulder 3.1.2. In an exemplary embodiment, a small diameter neck 3.1.3 projects distally from the shoulder 3.1.2 and is provided with a large diameter annular bead 3.1.4 extending circumferentially. A pierceable septum 3.1.5 extends across the open distal end 3.1.1 defined by the neck 3.1.3. The septum 3.1.5 is held in place by a ferrule 3.1.6 which is crimped around the annular bead 3.1.4 at a distal end of the neck 3.1.3.

The medicament M is pre-filled into the cartridge body 3.1 and is retained therein by a stopper 3.2. The stopper 3.2 is slidably movable within an inner wall of the cartridge body 3.1, wherein the inner wall of the cartridge body 3.1 is coated with a sliding layer 3.4 that may comprise silicon oil to enable an easy sliding of the stopper 3.2 on the inner wall of the cartridge body 3.1.

The stopper 3.2 comprises a rigid body 3.2.1 with a proximal end 3.2.1.1, a distal end 3.2.1.2 and a length that extends along the longitudinal axis A. A diameter of the rigid body 3.2.1 is smaller than an inner diameter of the cartridge body 3.1, thus the rigid body 3.2.1 alone cannot seal against the inner wall of the cartridge body 3.1. The rigid body 3.2.1 is made from a hard plastic material such as polypropylene, polyethylene, polyoxyethylene, polyamide or cyclo-olefin-copolymer.

The stopper 3.2 further comprises a soft sealing component 3.2.2 that slides on the inner wall of the cartridge body 3.1 during an injection process. In the shown exemplary embodiment, the soft sealing component 3.2.2 comprises two sealing portions 3.2.2.1, 3.2.2.2, each forming a ring around the circumference of the rigid body 3.2.1, wherein the sealing portions 3.2.2.1, 3.2.2.2 are spaced from each other in the direction of the longitudinal axis A. Alternatively, the soft sealing component 3.2.2 comprises only one of the sealing portions 3.2.2.1, 3.2.2.2 or more than two sealing portions 3.2.2.1, 3.2.2.2.

The sealing portions 3.2.2.1, 3.2.2.2 are made from a resilient material such as natural rubber or synthetic rubber for a fluid-tight engagement of the stopper 3.2 within the cartridge body 3.1.

The provided two-component stopper 3.2 requires low injection force, particularly when delivering high concentrated medicaments M, and high elasticity of the stopper 3.2 for a fluid-tight engagement of the stopper 3.2 within the cartridge body 3.1.

The medicament delivery device 1 further comprises a piston rod 3.3 that is movable along the longitudinal axis A with respect to the cartridge body 3.1 and that is coupled to the stopper 3.2 for moving the stopper 3.2 in the distal direction D within the cartridge 3, thus dispensing the medicament dose through a hollow needle 5 into a patient. Therefore, the piston rod 3.3 is coupled to the dial knob 4 that transfers a movement to the piston rod 3.3 when a user presses the dial knob 4 into the distal direction D. In case of using Insulin as the medicament, the movement of the piston rod 3.3 and consequently the stopper 3.2 for single dose increments could be less than 0.15 mm.

The needle 5 is pierced through the septum 3.1.5 and comprises a proximal tip 5.1 and a sharp distal tip 5.2. The proximal tip 5.1 is in fluid communication with the medicament M contained in the cartridge body 3.1, wherein the sharp distal tip 5.2 has to be inserted into a patient's skin for medicament delivery.

The stopper 3.2 may likewise be applied in a medicament cartridge 3 arranged as a syringe with a fixed injection needle 5.

Figure 2:
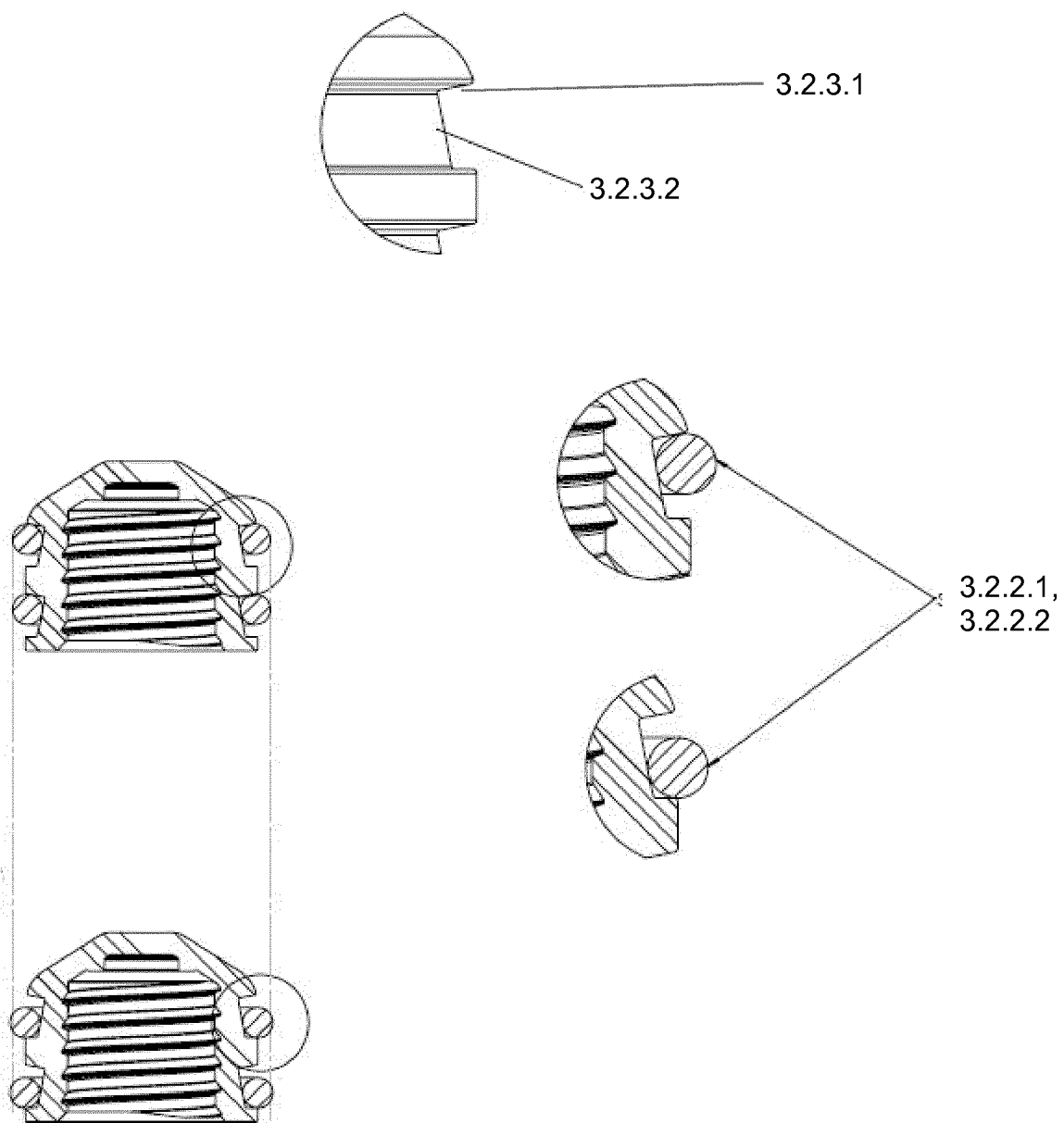
FIG. 2 shows a schematic longitudinal section of an exemplary embodiment of a stopper.

FIG. 2 shows a schematic longitudinal section of an exemplary embodiment of a stopper. Also shown is an example placement of the soft sealing component. Groove 3.2.3.1 holds the soft sealing components in their place but allows some movement for said components. This is to allow the said components to adjust to the actual friction between sliding layer 3.4 and sealing portions 3.2.2.1 and 3.2.2.2. The bottom of groove 3.2.3.1 has a slope 3.2.3.2 which is an additional means to keep the friction constant during gliding.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(02)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group-Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (02)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra-low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES 1 medicament delivery device
2 case
2.1 proximal end
2.2 distal end
2.3 dose window
3 medicament cartridge
3.1 cartridge body
3.1.1 distal end
3.1.2 shoulder
3.1.3 neck
3.1.4 annular bead
3.1.5 septum
3.1.6 ferrule
3.2 stopper
3.2.1 rigid body
3.2.1.1 proximal end
3.2.1.2 distal end
3.2.2 soft sealing component
3.2.2.1 sealing portion
3.2.2.2 sealing portion
3.2.3.1 groove
3.2.3.2 slope
3.3 piston rod
3.4 sliding layer
4 dial knob
5 needle 5.1 proximal tip
5.2 sharp distal tip
A longitudinal axis
D distal direction
M medicament
P proximal direction

The invention claimed is:

1. A medicament delivery device, comprising:
   a medicament cartridge containing a medicament; and
   a stopper slidably arranged within the medicament cartridge, wherein the stopper comprises a rigid body that is enclosed partially by a soft sealing component,
   wherein the soft sealing component comprises at least one sealing portion that forms a ring around a circumference of the rigid body, and the soft sealing component is arranged in a groove in a manner such that the soft sealing component is movable within the groove,
   wherein the groove has a groove bottom that is sloped with respect to a longitudinal axis of the medicament cartridge.

2. The medicament delivery device according to claim 1, wherein the rigid body comprises a hard plastic material.

3. The medicament delivery device according to claim 2, wherein the rigid body comprises polypropylene, polyethylene, polyoxymethylene, polyamide or cyclo olefin copolymer.

4. The medicament delivery device according to claim 1, wherein a diameter of the rigid body is smaller than an inner diameter of the medicament cartridge.

5. The medicament delivery device according to claim 1, wherein the soft sealing component comprises two sealing portions, each forming a ring around the circumference of the rigid body, wherein the sealing portions are spaced from each other in a direction of the longitudinal axis of the medicament cartridge.

6. The medicament delivery device according to claim 5, wherein the slope is oriented such that a depth of the groove bottom decreases from a distal end of the stopper to a proximal end of the stopper.

7. The medicament delivery device according to claim 1, wherein the soft sealing component is made from a resilient material.

8. The medicament delivery device according to claim 7, wherein the soft sealing component is made from natural rubber or from synthetic rubber.

9. The medicament delivery device according to claim 1, wherein the medicament cartridge comprises glass.

10. The medicament delivery device according to claim 1, wherein an inner wall of the medicament cartridge is coated with a sliding layer.

11. The medicament delivery device according to claim 10, wherein the sliding layer comprises silicon oil.

12. The medicament delivery device according to claim 1, wherein the medicament is insulin.

13. The medicament delivery device according to claim 1, wherein the soft sealing component is translatable within the groove along an axial direction.

14. The medicament delivery device according to claim 1, wherein an axial length of the groove is greater than a diametrical dimension of the soft sealing component.

15. The medicament delivery device according to claim 14, wherein the axial length of the groove is less than twice the diametrical dimension of the soft sealing component.

16. The medicament delivery device according to claim 1, wherein a cross section of the soft sealing component is circular.

17. The medicament delivery device according to claim 1, wherein the soft sealing component forms a fluid-tight engagement of the stopper within the medicament cartridge.

18. The medicament delivery device according to claim 1, further comprising a needle.

19. The medicament delivery device according to claim 18, further comprising a pierceable septum configured to be pierced by the needle.

* * * * *